United States Patent
Mannuzza et al.

(10) Patent No.: US 6,740,501 B2
(45) Date of Patent: May 25, 2004

(54) COATED MEMBRANE FOR ASSESSING THE INVASIVE CAPACITY OF A CELL

(75) Inventors: Frank J. Mannuzza, Chelmsford, MA (US); Paula Flaherty, Tyngsboro, MA (US); Stephen R. Ilsley, Boston, MA (US); Martin L. Kramer, Needham, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/942,349

(22) Filed: Aug. 29, 2001

(65) Prior Publication Data

US 2002/0119560 A1 Aug. 29, 2002

Related U.S. Application Data

(60) Provisional application No. 60/235,712, filed on Sep. 27, 2000.

(51) Int. Cl.[7] .................................................. C12Q 1/02
(52) U.S. Cl. ........................ 435/29; 435/34; 435/287.9
(58) Field of Search ........................... 435/29, 34, 287.9

(56) References Cited

U.S. PATENT DOCUMENTS

| | | | | |
|---|---|---|---|---|
| 4,829,000 A | * | 5/1989 | Kleinman et al. | ..... 435/240.23 |
| 5,714,465 A | * | 2/1998 | Langley et al. | ............... 514/12 |
| 6,087,157 A | * | 7/2000 | Badylak et al. | .......... 435/289.1 |

OTHER PUBLICATIONS

Bouchara J. P. Recognition of Fibrinogen and Basement Membrane Components as Mediators of the Adherence of A. fumigatus Conidia. Colloids and Surfaces B: Biointerefaces 2(1–3)299–304, 1994.*

Isley, Stephen R., "MATRIGEL® Basement Membrane Cell Invasion Chamber", Becton Dickinson Technical Bulletin #422 (1996).

Isley, Stephen R. et al., "An Improved MATRIGEL® Invasion Chamber", Becton Dickinson Technical Bulletin #427 (1998).

Flaherty, et al, "Screening of Anti–Metastatic Compounds of using the BD BioCoat (TM) Fluroblok (TM) Invasion System", The Cell/Line BD Biosciences, vol. 11, No. 2, Jun. 2001, pp. 1–8.

* cited by examiner

Primary Examiner—Ralph Gitomer
(74) Attorney, Agent, or Firm—Nanette S. Thomas; Richard E. Brown; Anthony P. Venturino

(57) ABSTRACT

A porous membrane is coated with a composition which includes a reconstituted and aggregated extracellular matrix derived from the Englebreth-Holm-Swarm mouse tumor, a polyol and a pH 7.8–8.2 buffer. The coated membrane is dried, affixed to an insert portion of an assembly and received in a well of a multiwell tissue culture plate. The invention includes a method to make the coated membrane.

8 Claims, 5 Drawing Sheets

COATED MEMBRANE FOR ASSESSING THE INVASIVE CAPACITY OF A CELL

This application claims priority to 60/235,712 filed Nov. 27, 2000.

FIELD OF THE INVENTION

This invention relates to cell culture, and more particularly relates to an improved device for measuring invasion by a cell through an aggregated polymerized extracellular matrix, and method for formation of the device.

BACKGROUND

Invasion is the process of cell movement across the basement membrane barrier and/or through the interstitial tissue. Invasion takes place during malignant tumor cell metastasis and during normal physiological processes such as angiogenesis and wound healing.

In vitro assessment of the invasive property of a cell has conventionally been carried out by quantitatively measuring the ability of the cell to digest away components of a reconstituted basement membrane which mimics the barrier function of natural basement membrane. A reconstituted basement membrane which has been extensively used in invasion determinations has been isolated from the Englebreth-Holm-Swarm (EHS) mouse tumor and disclosed in U.S. Pat. No. 4,829,000 to Kleinmann et al. and in Technical Bulletin 427 entitled "An Improved MATRIGEL® Invasion Chamber" (Becton Dickinson and Co.) wherein MATRIGEL® is a registered trademark of Becton Dickinson and Co. for an EHS preparation.

Assays for invasion using prior art EHS compositions coated onto a support surface, usually a porous membrane, are subject to various deficiencies, most of which are associated with a non-uniform drying of the prior art coating solution onto the porous support surface. A particular problem consequent to uneven drying is discontinuous cell invasion manifested by a patterning effect, such as dots or concentric rings of invading cells. Uneven drying may also lead to deposition of salt crystals at the outer edges of the membrane due to surface tension effects and an unacceptable number of uncoated pores. Because of these and other deficiencies with prior art coatings, discrimination between invasive and non-invasive cells may be compromised.

SUMMARY OF THE INVENTION

A porous membrane for determining invasivity of a cell has a composition thereon which includes a coating of reconstituted extracellular matrix derived from the EHS mouse tumor. The composition is applied with a coating solution which includes a polyol in a pH 7.8–8.2 buffer. The preferred buffer is Tris and the preferred polyol is sucrose.

A second aspect of the invention is an assembly which includes a multiwell tissue culture plate and an insert having a sleeve therethrough. The sleeve mates with a well of the plate, and the coated membrane serves as the bottom wall of the sleeve. The assembly may optionally include a lid for the plate and a feeder tray.

Another aspect of the invention is a method to prepare the coated membrane. The method includes inducing aggregation of components of the EHS and drying and stabilizing the composition on the porous membrane.

There is a need in the art for a composition which forms a uniform coating on a porous support, which is highly digested by an invasive cell substantially resistant to passage of a non-invasive cell and which thereby provides an easy and accurate discrimination between invasive and non-invasive cells. The present invention is directed to fulfilling this need.

DETAILED DESCRIPTION

Figure 1:
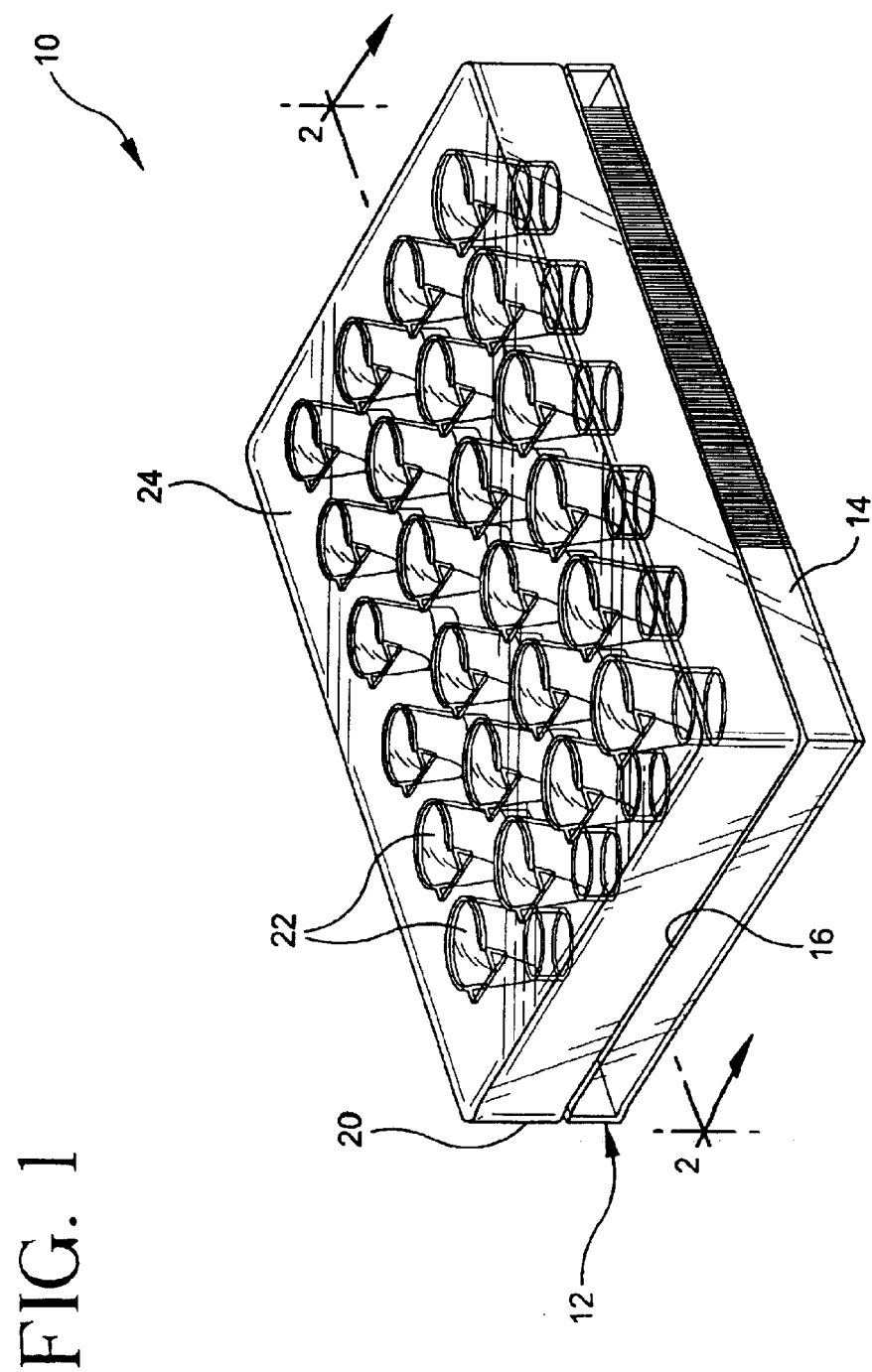
FIG. 1 is a top perspective view of a multi-well analysis assembly useful as an invasion chamber for determining cell invasion through an extra-cellular matrix.

While this invention is satisfied by embodiments in many different forms, there will herein be described in detail embodiments of the invention with the understanding that the present disclosure is to be considered as exemplary of the principles of the invention and is not intended to limit the invention to the embodiments illustrated and described. The scope of the invention will be measured by the appended claims and their equivalents.

Basement membranes are delicate connective tissues which underlie the epithelium of many organs. The composition of the invention is a reconstituted basement membrane which mimics the activity of the natural membrane and provides cells with an environment conducive to growth, attachment or penetration. When coated on a suitable support and used with commercially available cell culture equipment, as described below, the composition is suitable for either manual or robotic screening of cells in bioavailability, toxicity and migration studies, and is ideally suited for assessment of the invasive capacity of a cell.

The composition of the invention may be applied in buffer solution to any porous surface, hereinafter referred to as the support surface, intended for contact with cells. The porous support surface may be of any suitable material, such as glass and ceramic. Preferred support surfaces are polymeric such as for example, polyvinyl chloride, polyolefin, polystyrene (PS), polycarbonate, and preferably polyethyleneterephthalate (PET). The polymeric support surface may be in the form of a porous film, which itself may be coated onto a support of other material. The most preferred support surface is a porous polymeric membrane, and the invention will hereinafter be described in detail for a porous PET membrane support surface. The most preferred porous membrane is of track-etched PET and may be about 0.5 to 30, preferably about 8 um thick and have pores of 3–12 um in diameter.

A first component of the composition is a reconstituted extracellular matrix derived from the EHS mouse tumor. This matrix, hereinafter referred to as EHS in this disclosure, is well known in the art, is fully disclosed in the aforementioned U.S. Pat. No. 4,829,000 and is sold by Becton Dickinson and Co. under the trademark MATRIGEL®.

The EHS may be dissolved in a buffer which provides a pH of 7.8 to 8.2, preferably about 8.0. Any buffer as known in the art which provides this pH range may be used, as for example, diethanolamine, N-ethylmorpholine, triethanolamine, N,N-bis (2 hydroxyethyl glycine) and dimethylleucyl glycine. The preferred buffer is Tris [tris (hydroxymethyl) aminomethane, TRIZMA®], and may be used at a concentration of 0.01 to 0.05M. The concentration of EHS dissolved in the buffer solution is 60–100 ug/cm$^2$ of membrane surface to be coated.

The composition also includes a salt (preferably sodium chloride) added to the buffer to keep the EHS in solution. The salt may be used at 0.08 to 0.15M in the buffer.

A polyol at 2–8 gm% is added to the EHS solution. Suitable polyols are sugars, glycols and polymers and copolymers thereof, such as monosaccharides, disaccharides, oligosaccharides, dextrans, polyalkylene glycols, and polymers and copolymers thereof. The preferred polyol is sucrose.

The solution described above, maintained at 0–10° C., may be applied to either or both of the upper and lower surfaces of the membrane, preferably through a micropipette, at concentrations of from 10–150, preferably 65–105 ug/cm$^2$ of membrane surface in such a way that the entire membrane surface is covered.

The coated membrane may then be incubated at a temperature of 15–40, preferably 33–40° C. for 1–4 hrs at 40–60% relative humidity to induce aggregation of components of the EHS and adherence of the aggregate to the membrane. Finally, the aggregate on the membrane surface may be stabilized and dried to prevent any disruption of the aggregate and preserve the even coating. Any procedure as known in the art which avoids vibrational disturbance of the coating may be used for this step. A preferred technique is drying in a controlled environment, most preferably at a temperature of 20–32° C. and relative humidity of 40–60%.

The preferred embodiment of the invention is given in the following chart, with various parameters compared with the closest prior art.

be included in an assembly for studies of cell attachment, growth and invasion. The assembly may include a multiwell tissue culture plate and insert therefor. The insert may have openings defined by vertical side walls which form open ended sleeves fitting within the wells of the plate. Tissue culture plate assemblies are conventional in the art and are exemplified by the multiwell plate and insert system sold by Becton Dickinson and Co. under the trade name FALCON® In the instant assembly, the membranes coated with the composition of the invention as described above serve as the bottom walls of the insert sleeves.

Figure 2:
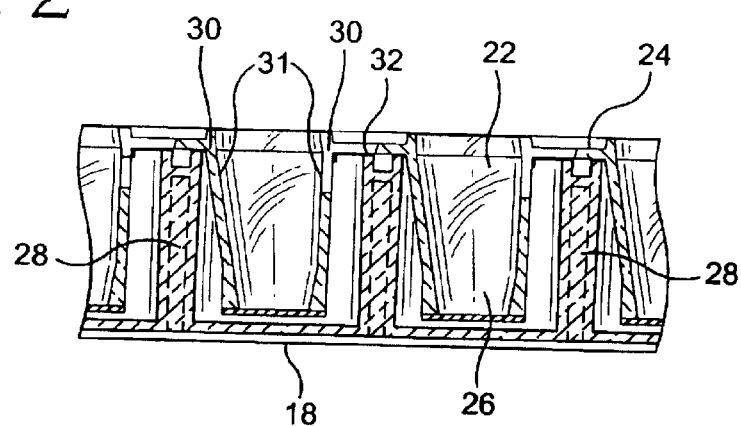
FIG. 2 is a cross-sectional view of the assembly of FIG. 1 taken along line 2—2 of FIG. 1.

Adverting now to the drawings, wherein like elements have the same reference number followed by a lower case letter suffix, FIGS. 1 and 2 illustrate a multi-well assembly 10 for cell analysis. Assembly 10 includes a generally rectangular plate 12. Plate 12 has a side wall 14, a top edge 16 and a horizontal bottom wall 18. An insert 20 fits within the plate 12 and has a plurality of openings 22 through a deck 24.

In FIG. 2, a plurality of wells 26 defined by vertical walls 28 project upwardly from the horizontal bottom wall 18. Openings 22 of the insert are defined by vertical walls 30 projecting downwardly from deck 24. Vertical walls 30 form a sleeve 31 have 2 open ends. Wells 26 are dimensioned to receive sleeve 31 therein with deck 24 resting on the top 32 of well walls 28.

Figure 3:
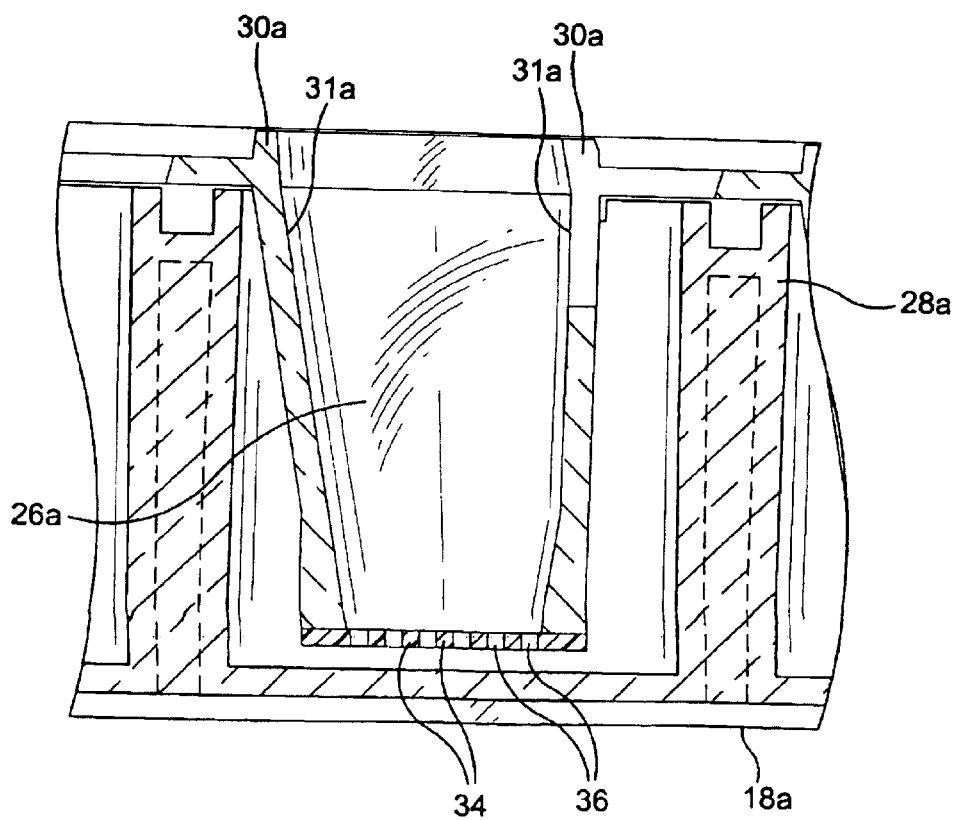
FIG. 3 is an enlarged cross-sectional view of one well of the assembly of FIG. 2.
Figure 4:
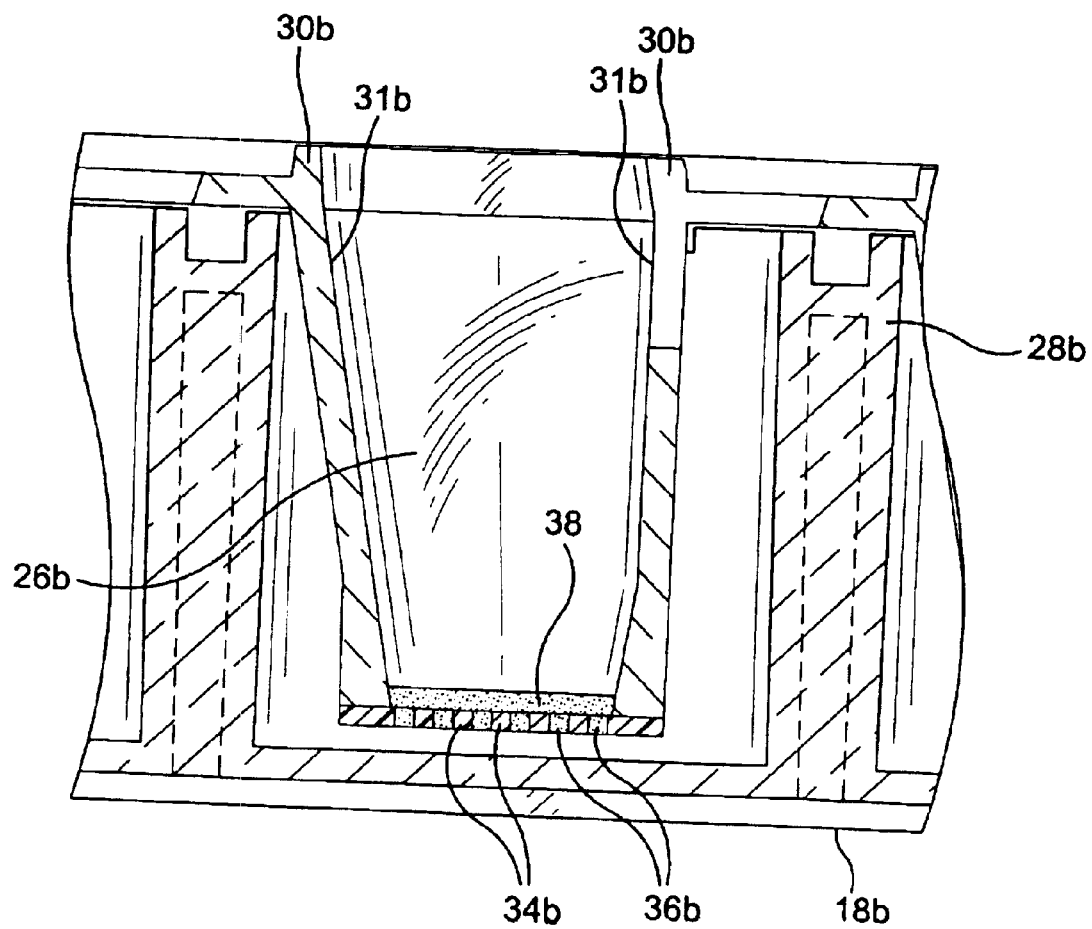
FIG. 4 is an enlarged cross-sectional view of the well of FIG. 3 after coating with the composition of the invention.

FIGS. 3 and 4 are enlarged illustrations of one well (26a) of the assembly of FIG. 2 showing a porous membrane 34 having pores 36 therethrough, extending across and providing a bottom wall for sleeve 31a. FIG. 4 shows aggregated coating composition 38 of the invention on the surface of membrane 34b and pores 36b. Visual inspection shows the coating of the invention to be smooth, glossy and even, and that pores 36b are substantially all closed.

Figure 5:
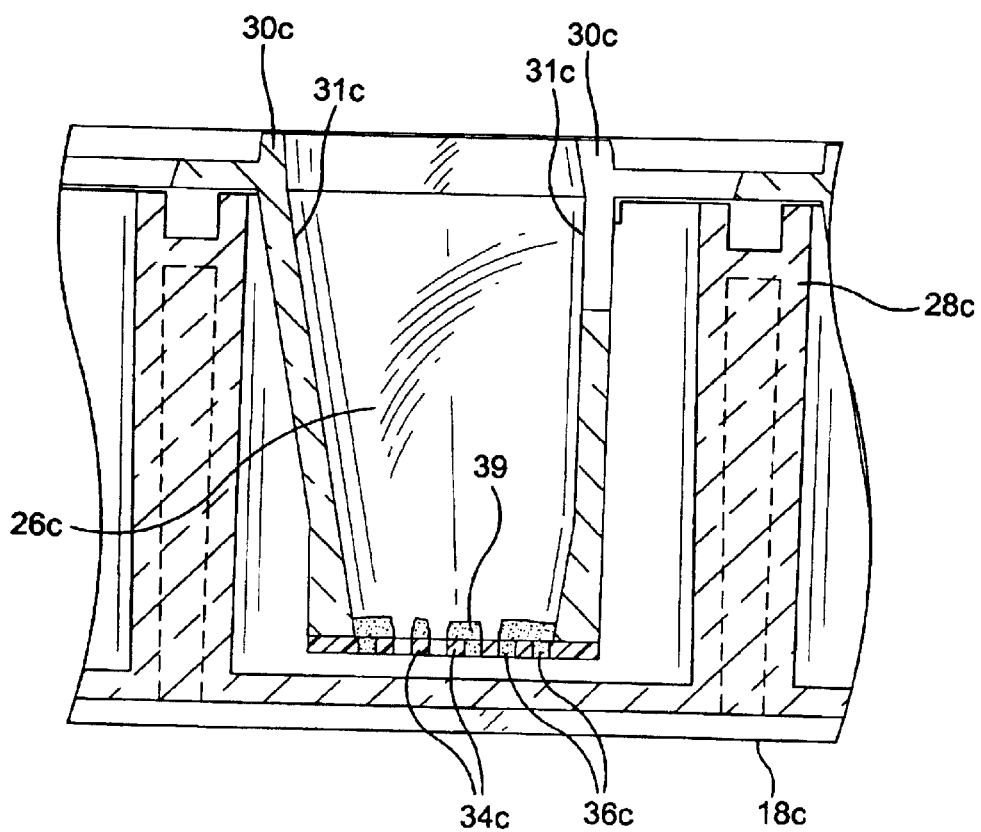
FIG. 5 is an enlarged cross-sectional view of one well of the assembly after coating with a prior art composition.

FIG. 5 shows the coated surface of the membrane after coating with the prior art composition. Inspection of this coating (39) shows a hazy, uneven surface, with a substantial number of open (unclosed) pores.

| | | Prior Art | Invention |
|---|---|---|---|
| a) | Composition of coating solution | | |
| i) | EHS | 85 ug/cm$^2$ | 85 ug/cm$^2$ |
| ii) | Diluent | Phosphate buffered saline pH 7.4 | Tris/saline pH 8.0 with 4% sucrose |
| iii) | Temperature | Held on ice | Held on ice |
| b) | Volume of coating solution (24-well insert) | 100 ul | 100 ul |
| c) | Aggregating conditions | 37° C., 50% RH 120 minutes | 37° C., 50% RH, 120 min. |
| d) | Drying conditions | 20–24 hours 30° C., 50% RH | 20–24 hours 30° C., 50% RH |
| e) | Packaging and storage | Foil, −20° C. | Foil, −20° C. |
| f) | Appearance | Overall hazy appearance with salt crystals at periphery | Overall clear glossy or wet appearance |
| g) | Stability | Unstable after 1 week at 4° C. | Stable for at least 4 weeks at 4° C. |
| h) | Invasion pattern of cells | No invasion at periphery, often bulls eye appearance | Even invasion throughout entire surface of insert |
| i) | Acceptable membrane lots* | Less that 50% can be used | Greater than 90% can be used |
| j) | Acceptable EHS lots* | Less than 20% | Greater than 80% |

*meets performance specification-see below

Figure 6:
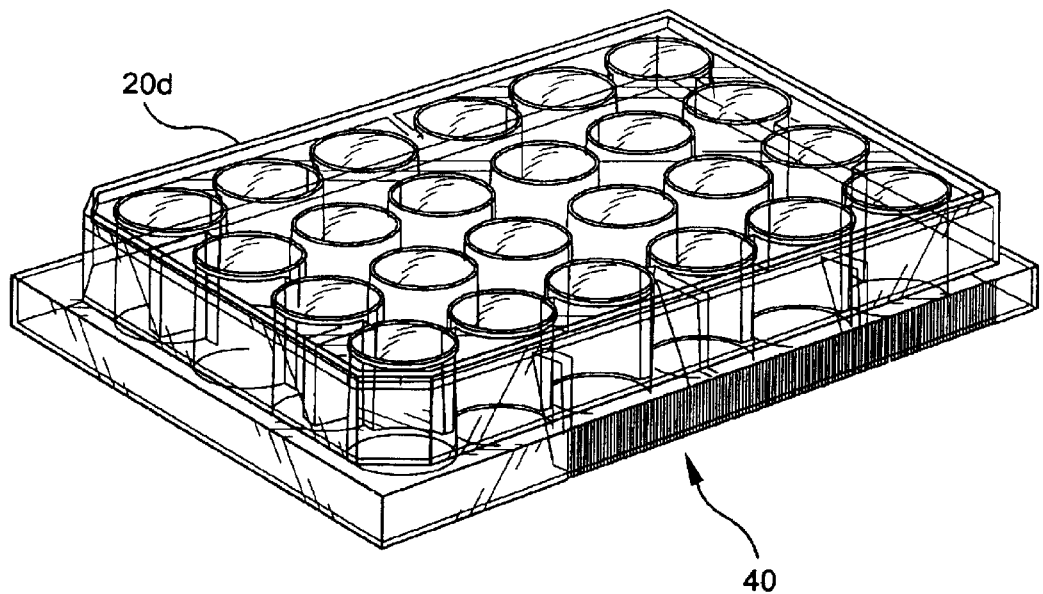
FIG. 6. is a top perspective view of a feeder tray of the assembly.
Figure 7:
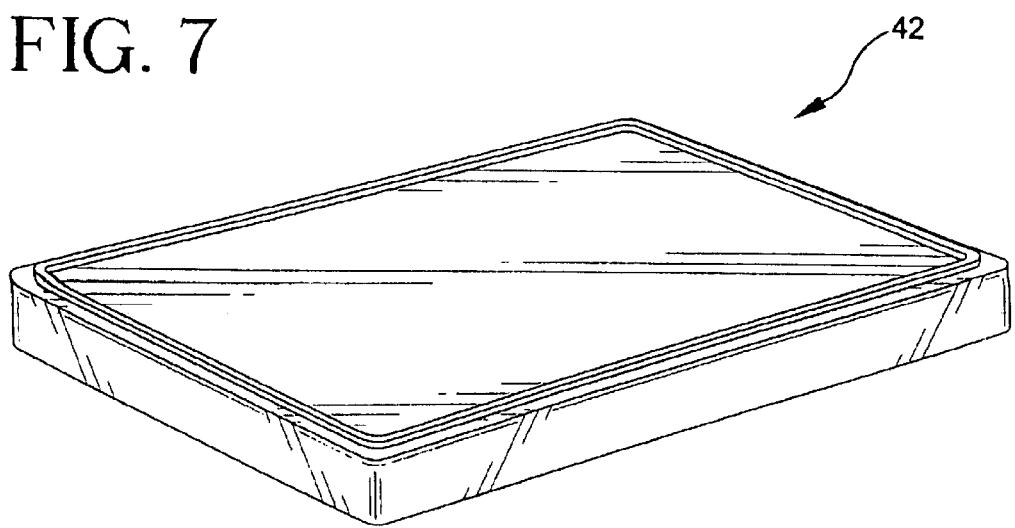
FIG. 7 is a top perspective view of a lid of the assembly.

In another aspect of the invention, the membrane coated with the composition of the invention may advantageously The assembly may include a plastic, preferably PS, feeder tray 40 (FIG. 6) dimensioned to receive the insert and thereby provide a receptacle capable of bathing the membrane of all wells simultaneously in the same medium. In addition, the assembly may contain a lid (42, FIG. 7) preferably of PET, dimensioned to cover the insert in either the plate or feeder tray to provide a sealed environment for storage or incubation periods.

In accordance with the invention, the invasive capacity of a cell can be quantitatively measured by the extent of its invasion through the coated membrane of the invention. Using NIH cell line 3T3 as a typical non-invasive cell and HT-1080 as a typical invasive cell, the coated membrane of the invention allowed high discrimination between the two cell types, and met the following desired performance specification:

3T3–10% or less invasion.

HT-1080–25% or greater invasion, with invading cells evenly distributed across the surface of the membrane and no significant patterning.

It has been found that the sucrose in the composition of the invention prevents the crystallization of the salt, allowing a more uniform distribution of both salts and protein (EHS) on the upper surface of the membrane. This uniform distribution of the protein provides even invasion by the cells through the membrane resulting in even distribution of invaded cells on the underside of the membrane. This data is shown in Table 1 of Example 2.

The pH of the coating solution was found to have a dramatic controlling effect on the generation of aggregates that both adhere to the membrane surface and occlude the membrane pores. At low pH, pores were much less occluded by the composition than at more alkaline pH. It is believed, but not fully established, that this effect is due to aggregate size. This data is summarized in Table 2 of Example 2.

An added advantage of the coated membrane of the invention is a markedly improved shelf life compared to prior art membranes.

EXAMPLE 1

Preparation of Membrane

A. Preparation of Coating Solution.

Sucrose at 2–8 gm% was added to Tris buffer (0.01–0.05 m) at pH 7.8–8.2 containing 0.08–0.15 m NaCl. While maintaining this solution at 0–10° C., sufficient EHS was added to yield 10–150, preferably 65–105 ug per cm$^2$ of membrane surface to be coated. The coating solution thus prepared was maintained at 0–10° C.

B. Coating Procedure

The coating solution prepared above was applied with a micropipette onto a track-etched PET membrane having 8 um pores. The coating was applied either prior to and subsequent to affixing the membrane across the open ends of the sleeve portion of the FALCON® insert, care being taken to apply an even coating of solution over the entire membrane surface. The coated membrane was held at 33–40° C. and 40–60% relative humidity for 1–3 hours to aggregate the EHS components. The aggregated coating was stabilized by drying at 25–30° C. and 40–50%RH, and the insert stored at 4° C. or lower, preferably at −20° C.

EXAMPLE 2

Method For Assay of Cell Invasion

The membrane coated with the composition of the invention and prior art membranes were tested for cell invasion by the procedure set forth in Technical Bulletin 427 supra. Percent invasion was determined by staining (preferably with coomassie blue) and counting the cells by conventional Q PC-172 or DNA measurement on the underside of the membrane. The following results were obtained:

Effect of Sucrose (% invaded cells):

TABLE I

| DILUENT | Lot [a]1 | | Lot 2 | | Lot 3 | | Lot 4 | |
|---|---|---|---|---|---|---|---|---|
| | 3T3 | HT[b] | 3T3 | HT | 3T3 | HT | 3T3 | HT |
| DPBS | 25 | 92 | 19 | 100 | 16 | — | 29 | 92 |
| DPBS-S[c] | 77 | — | 57 | 85 | — | — | 79 | 98 |
| TS | 4 | 40 | 1 | 40 | 1 | 73 | 4 | 51 |
| TS-S[d] | 15 | 95 | 15 | 99 | 10 | 99 | 24 | 92 |

[a]lot of MATRIGEL ®
[b]HT-1080
[c]Dulbecco's phosphate buffered saline-4% sucrose
[d]Tris saline-sucrose

TABLE 2

| | Effect of pH | |
|---|---|---|
| PH | 3T3 | HT 1080 |
| 6.0 | +++ | +++ |
| 6.5 | ++ | +++ |
| 7.5 | ++ | +++ |
| 8.0 | ± | +++ |
| 8.5 | ± | ±+ |

+++ high % invasion
++ moderate invasion
+ low invasion
_ little or no invasion

EXAMPLE 3—COMPARATIVE

A membrane in accordance with the prior art using Tris buffer but without sucrose met the performance specifications with respect to percent cell invasion by 3T3 and HT1080, but gave a grossly uneven distribution of invaded cells which were difficult to count.

EXAMPLE 4—COMPARATIVE

A membrane in accordance with the prior art using sucrose in a phosphate buffer formulation (pH 7.4) gave an unacceptably high percent of uncoated pores as measured by the migration through these pores by a non-invading cell line.

What is claimed is:

1. A coated membrane for assessing the invasive capacity of a cell comprising;

a) a porous membrane; and b) a composition on a surface of said membrane, said composition comprising a reconstituted and aggregated extracellular basement membrane matrix derived from Englebreth-Holm-Swarm mouse tumor, a pH 7.8 to 8.2 buffer and a polyol.

2. The coated membrane of claim 1 wherein said porous membrane is a polymer.

3. The coated membrane of claim 1 wherein said polyol is selected from the group consisting of a sugar, glycol and polymers and copolymers thereof.

4. The coated membrane of claim 1 wherein said buffer comprises an aminoalcohol.

5. The coated membrane of claim 1 further comprising a salt.

6. The coated membrane of claim 1 which has been dried.

7. The coated membrane of claim 1 wherein said reconstituted and aggregated extracellular basement membrane matrix is an aggregated polymerized extracellular matrix.

8. A coated membrane for assessing the invasive capacity of a cell comprising:

a) a polyethyleneterephthalate porous membrane; and b) a composition on a surface of said membrane, said composition comprising a reconstituted and aggregated extracellular basement membrane matrix derived from Englebreth-Hoim-Swarm mouse tumor, a pH 7.8–8.2 buffer comprising tris (hydroxymethyl) aminomethane, salt and sucrose.

* * * * *